(12) United States Patent
Ruijters et al.

(10) Patent No.: US 10,803,632 B2
(45) Date of Patent: Oct. 13, 2020

(54) IMAGE PROCESSING SYSTEM FOR ELIMINATING OR REDUCING STREAK ARTIFACTS IN ROTATIONAL IMAGING

(71) Applicant: KONINKLIJKE PHILIPS N.V., Eindhoven (NL)

(72) Inventors: Daniël Simon Anna Ruijters, Eindhoven (NL); Thijs Grunhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 164 days.

(21) Appl. No.: 16/062,068

(22) PCT Filed: Dec. 14, 2016

(86) PCT No.: PCT/EP2016/081073
§ 371 (c)(1),
(2) Date: Jun. 13, 2018

(87) PCT Pub. No.: WO2017/102887
PCT Pub. Date: Jun. 22, 2017

(65) Prior Publication Data
US 2018/0365869 A1    Dec. 20, 2018

(30) Foreign Application Priority Data
Dec. 15, 2015    (EP) .................................. 15200072

(51) Int. Cl.
*A61B 5/00*    (2006.01)
*A61B 6/03*    (2006.01)
*G06T 11/00*    (2006.01)
*A61B 6/00*    (2006.01)

(52) U.S. Cl.
CPC ............ *G06T 11/005* (2013.01); *A61B 5/742* (2013.01); *A61B 6/032* (2013.01); *A61B 6/4085* (2013.01); *G06T 11/008* (2013.01)

(58) Field of Classification Search
None
See application file for complete search history.

(56) References Cited

U.S. PATENT DOCUMENTS

| 8,023,767 | B1 | 9/2011 | Ning et al. |
| 2005/0053184 | A1 | 3/2005 | Bijjani |
| 2006/0039537 | A1 | 2/2006 | Strobel |
| 2011/0107270 | A1 | 5/2011 | Wang |
| 2013/0070991 | A1 | 3/2013 | Yang et al. |

(Continued)

FOREIGN PATENT DOCUMENTS

| CN | 103617598 A | 3/2014 |
| JP | 2001286463 A | 10/2001 |

(Continued)

*Primary Examiner* — Idowu O Osifade

(57) ABSTRACT

An image processing system, comprising an input port (IN) for receiving a projection image of an object. The image is acquired by a rotational image apparatus (IM) at a position on an imaging trajectory in an adjustable rotation plane (π) around an imaging region. An image artifact extent predictor (AP) of the system is configured to predict for said image a projection area of a reconstruction artifact. A visualizer (VIZ) is configured to visualize, on a display unit (MT), said image with a visual indication of the projection area.

14 Claims, 7 Drawing Sheets

(56) References Cited

U.S. PATENT DOCUMENTS

| | | | |
|---|---|---|---|
| 2014/0169650 A1 | 6/2014 | Sakimoto et al. | |
| 2015/0305702 A1 | 10/2015 | Sakimoto et al. | |
| 2017/0135665 A1* | 5/2017 | Sandholm | A61B 6/469 |

FOREIGN PATENT DOCUMENTS

| | | | |
|---|---|---|---|
| JP | 2003135450 A | 5/2003 | |
| JP | 2010099303 A | 5/2010 | |
| JP | 2014226321 A | 12/2014 | |
| WO | 2010038195 A2 | 4/2010 | |
| WO | 2011105472 A1 | 9/2011 | |
| WO | 2012056379 A1 | 5/2012 | |
| WO | 2013061239 A2 | 5/2013 | |
| WO | 2014137353 A1 | 9/2014 | |

* cited by examiner

A)

B)

IMAGE PROCESSING SYSTEM FOR ELIMINATING OR REDUCING STREAK ARTIFACTS IN ROTATIONAL IMAGING

CROSS-REFERENCE TO PRIOR APPLICATIONS

This application is the U.S. National Phase application under 35 U.S.C. § 371 of International Application No. PCT/EP2016/081073, filed on Dec. 14, 2016, which claims the benefit of European Patent Application No. 15200072.5, filed on Dec. 15, 2015. These applications are hereby incorporated by reference herein.

FIELD OF THE INVENTION

The invention relates to an image processing system, to an imaging arrangement, to an image processing method, to a computer program element, and to a computer readable medium.

BACKGROUND OF THE INVENTION

The presence, during imaging, of a highly radiopaque object (e.g. a metal object) may cause so-called streak artifacts in rotational tomographic imaging. Such artifacts can obscure clinically relevant information. This is a problem for instance in interventional (stent-assisted) coiling procedures: after a (metallic) coil has been placed to treat aneurysms, the metal coil may cause severe streak artifacts in a reconstructed cone-beam CT (CBCT) image, potentially obscuring clinically relevant details, e.g., the stent-vessel wall interface.

SUMMARY OF THE INVENTION

There may therefore be a need for a system and method to deal with image artifacts in rotational imaging.

The object of the present invention is solved by the subject matter of the independent claims where further embodiments are incorporated in the dependent claims. It should be noted that the following described aspect of the invention equally applies to the image processing method, to the imaging arrangement, to the computer program element and to the computer readable medium.

According to a first aspect of the invention there is provided an image processing system, comprising:

an input port for receiving a projection image of an object, the image acquired by a rotational image apparatus at a position on an imaging trajectory in a first rotation plane ($\pi$) around an imaging region;

an image artifact extent predictor configured to predict for said image a projection area of a reconstruction artifact, and an imaging geometry adjuster configured to determine a adjustment of a relative spatial configuration between said rotation plane and the object so as to reduce an intersection between the predicted projection area and an area in the image that corresponds to a predefined region of interest ROI.

In other words, an impact (extent and/or orientation) of the artifact relative to a region of interest (ROI) in a reconstruction is evaluated before doing a full rotational CBCT scan, thus avoiding unnecessary X-ray dosage. This allows avoiding imaging geometries that would result in reconstructions that are potentially useless as the ROI may turn out to be too severely compromised by the artifacts.

While inputting a single X-ray projection image to the input port of the proposed system may suffice, in an example a plurality of input images may be used as this allows further increasing the accuracy of the predicted area. Put differently, the proposed system allows simulating or trying different imaging geometry settings, without radiation exposure, until an imaging geometry is found which would result in a reconstruction where the ROI is less, or not at all, affected by the artifact(s). Based on the image processing, the system allows a user or a protocol to control the imaging geometry and use an alternative imaging trajectory.

A possible adjustment of said spatial configuration may be realized by defining an adjusted rotation plane having a different rotation axis than the current (first) rotation plane. Thus, by means of the imaging geometry adjuster, an adjustment of a rotational plane, in which a CBCT rotational scan will be carried out, with respect to the object to be imaged may be determined.

In an example, a tilt angle of the rotational plane may be increased or decreased so that a reconstruction from images of a CBCT scan to be carried out along a trajectory in the adjusted rotational plane would exhibit reduced image artefacts in the region of interest. The increasing or decreasing of the tilt angle may be determined automatically, for example image artefacts for a number of different adjusted rotational planes may be simulated and used to find a minimum in the intersection between their projection and the region of interest.

In addition or alternatively, a position or inclination of a support on which the object resides is changed.

In an embodiment, the system is provided with a visualizer configured to provide, to a display unit, image information representing the input image together with a visual indication of the projection area of the reconstruction artefact. The visualizer may also, in addition, display a visual indication of the projection area of the reconstruction artefact for one or more adjusted spatial configurations. Thus, a user may be enabled to try out various spatial configurations to find one in which reconstruction artefacts will be substantially reduced.

According to one embodiment, said reconstruction artifact is caused by a radio-opaque object, in particular a metal object, resident in the imaging region.

According to one embodiment, said specified change of the spatial configuration is effectuated by a human user.

According to one embodiment, a graphical user interface is provided that is configured to allow the user to graphically specify an adjustment of the relative spatial configuration between the object and the rotation plane. For this purpose, for example, the user may use the visual indication of the projection area of the reconstruction artefact and its intersection with the region of interest, as provided by the visualizer, as a guidance.

According to another aspect there is provided an imaging arrangement that comprises the image processing system as per any one above mentioned embodiments and said imaging apparatus and/or said display unit.

According to another aspect there is provided an image processing method, comprising:

receiving a projection image of an object, the image acquired by a rotational image apparatus at a position on an imaging trajectory in an adjustable rotation plane around an imaging region;

predicting for said image a projection area of a reconstruction artifact; and determining an adjustment of the relative spatial configuration between said rotation plane and the object so as to reduce an intersection between the predicted projection area and an area in the image that corresponds to a predefined region of interest.

In an embodiment, the predicting and determining step are repeated, with the aim of decreasing an image area of the intersection between the projection of the reconstruction artefact and the region of interest in an iterative process. For example, the steps may be repeated automatically until no artefact projection intersecting with the region of interest remains, or at least until a minimum size for the intersection area has been found if that proves to be not possible.

According to one embodiment, the method comprises operating the imaging apparatus to acquire projection images at different positions on the trajectory in accordance with the adjusted relative spatial configuration between the rotation plane and the object. In other words, a rotational CBCT image acquisition scan may be carried out. Then, from the acquired projection images, a volumetric image of at least the region of interest may be reconstructed.

In other words, in this embodiment, a reconstruction based on the projection images will yield volumetric imagery wherein the ROI is either not compromised at all by reconstruction artifact or is at least compromised up to a more acceptable level.

In a further embodiment, the new imaging geometry is selected so that any collision between C-arm, patient and table may be avoided. Thus, the selected trajectory may not reflect an absolute minimum in reconstruction artefacts interfering with the region of interest, but rather a relative minimum within the constraint of a collision-free movement of the imaging system being required.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
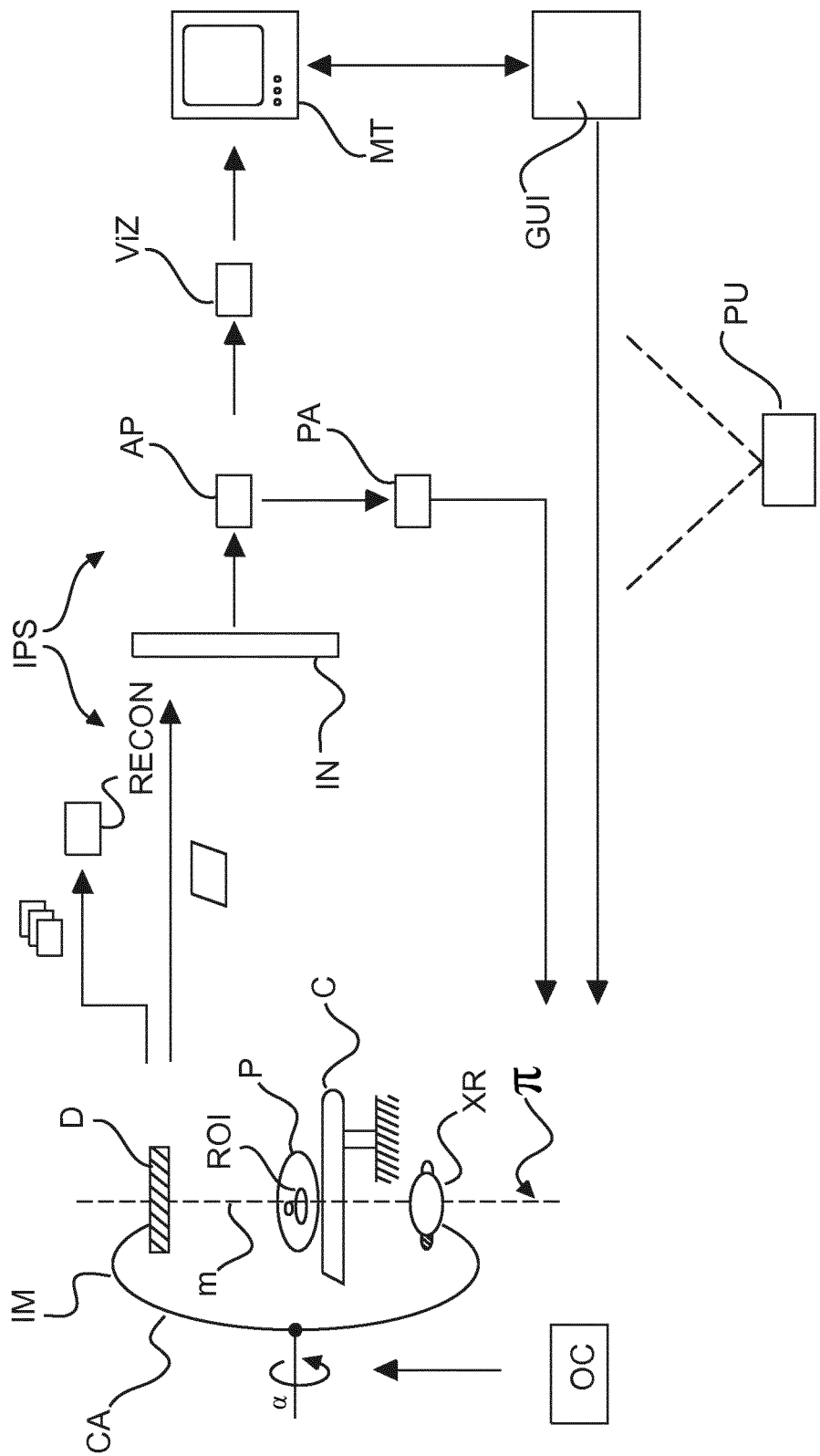
FIG. 1 shows a schematic block diagram of an imaging processing system.

With reference to FIG. 1, there is shown a schematic block diagram of an imaging arrangement including an imaging apparatus IM and an image processing system IPS.

More particularly, the left part of the Figure shows a rotational imaging apparatus IM such as a C-arm system or alternatively a CT scanner. The right part of FIG. 1 shows modules and related circuitry of the image processing system IPS. The image processing system IPS allows manual or automatic operation of the imaging apparatus IM so as to reduce effects of streak artifacts in imagery reconstructed from projection data acquired by the imaging apparatus IM.

Turning now first to a brief description of the imaging apparatus IM, this includes an X-ray source XR and a detector D. Being a rotational X-ray system, it is at least the X-ray source XR that is rotatable in a trajectory around an imaging region. The (rotation) plane of the trajectory is shown in FIG. 1 as a dashed line as said plane is understood to extend into the paper plane of the drawing. The trajectory may not necessarily be circular although this will be the case indeed in some preferred embodiments. Also it is not necessarily the case that the X-ray source orbits in a complete rotation around the imaging region. Indeed in some embodiments the trajectory defines only a partial arc such as 200° around the imaging region. In some embodiments such as the C-arm and most CT scanners it is the detector and the X-ray source that are arranged opposite each other whilst both rotate around the imaging region tracing out the imaging trajectory. In other embodiments such as fourth generation CT scanners it is only the X-ray source that is rotating whilst the detector is arranged as a stationery circular arrangement around the imaging region.

In the imaging region there is disposed an object or patient P (human or animal) on a suitable support C such as a couch. The imaging set-up is so arranged that the region of interest ROI is situated in the iso-center of the imaging trajectory. In rotational imaging one wishes to obtain a cross sectional image of the internals of the imaged object P. For present purposes, the imaged object P may be a human or animal patient or a particular part thereof. In order to produce such a cross sectional image, a series of projection images are acquired whilst the X-ray source traces out the trajectory around the imaging region and hence around the region of interest. In cone beam CT, particularly envisaged herein, a relatively large number (such as 600 or more) projection images are acquired.

These projection images can then be processed by a re-constructer component RECON. The re-constructer component RECON implements a reconstruction algorithm such as filtered back-projection or otherwise (such as iterative methods) to produce the cross sectional image.

In order to be able to acquire the most relevant projection images for a ROI, an orientation of the rotation plane it can be adjusted. More particularly a spatial configuration (also referred to herein as "imaging geometry") between the rotation plane and the object (and hence the ROI) can be changed. Yet more precisely and geometrically speaking, it is the rotation axis α of the rotation plane 7E that can be altered by operation of one or more suitable actuators. For instance, in one embodiment, the actuators (e.g., stepper motors etc.) cause a motion of a gantry C on which the X-ray source and/or the detector D are mounted and this motion effects the change of the rotation axis α of the rotation plane. Alternatively or in in addition, the spatial configuration between the rotation plane and the object P can also be changed by shifting or rotating the support C on which the object is deposed.

The change of the spatial configuration between the rotation plane and the object can be requested from an operator console OC. For instance in one embodiment the user can operate a joy-stick or other input device to effect suitable adjustments of the imaging geometry. In other embodiments the change of imaging geometry is requested automatically by an imaging protocol. In FIG. 1, the degrees of spatial freedom are shown at the example of a C-arm imager. The rotation of the X-ray source XR in rotation plane π around the imaging region and axis α is shown in FIG. 1. In the exemplary situation in schematic FIG. 1, the rotation axis α runs parallel to the plane of the drawing with the rotation plane π extending into the drawing plane. One possible way to change the rotation axis α is to rotate same out of the drawing plane, thereby defining a new rotation plane π' (not shown).

Figure 2:
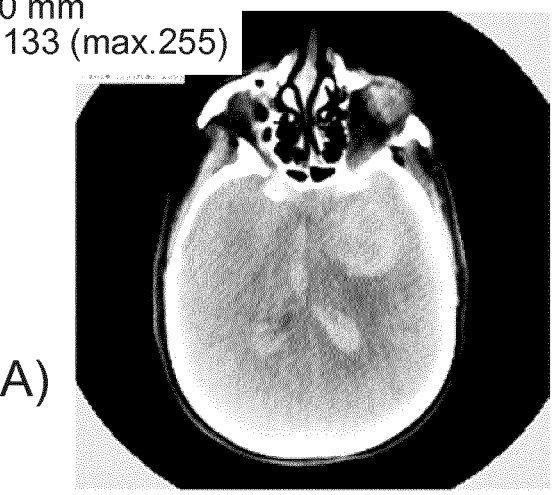
FIG. 2 shows reconstructed rotational imagery affected by reconstruction artifacts, in particular streak artifacts.
Figure 2:
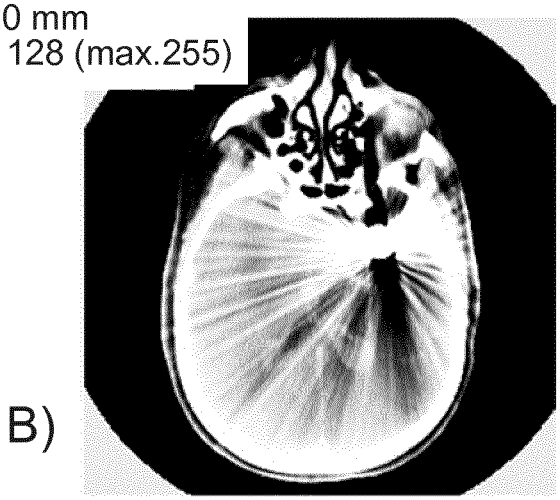
Figure 2:
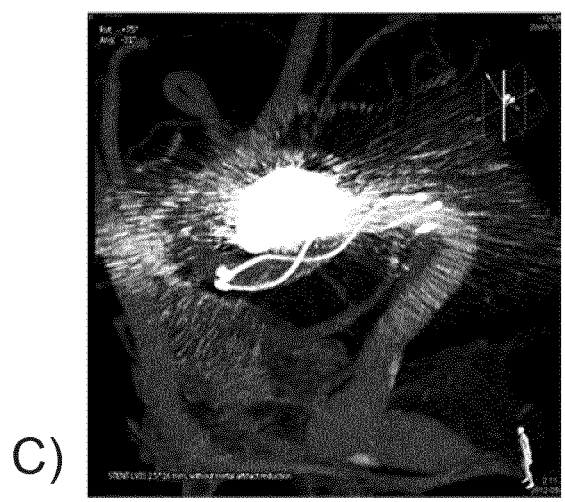

It is known that when there are highly radiation-opaque singularities such as metallic particles or objects (implanted stents, coils, pacemaker, etc.) embedded in surrounding tissue of lesser density, streak artifacts may occur in the reconstructed imagery. One reason for this is that the (relative to the surrounding tissue) highly radiation-opaque singularities cause photon starvation and changes in the spectrum of the X-ray radiation that passes through the object, an effect sometimes also referred to as "beam hardening" in rotational X-ray imaging. These phenomena violate the assumptions on which most reconstruction algorithms are based. The reconstruction algorithm attempts to find a suitable material distribution that fits the projection data. This process entails assigning individual image values to the respective voxel positions to so build up the distribution and thus the cross sectional image in a given plane. But, as noted above, the violation of the underlying assumptions in respect of the spectrum together with the photon starvation may cause the reconstruction algorithm to return an artificial material distribution that does not correctly describe the true material distribution thus producing streak artifacts that have a hedgehog-like appearance as shown in panes B),C) in the exemplary imagery in FIG. 2. Yet more particularly, the radiation opaque objects. The exemplary streak artifacts as shown in B), C) in FIG. 2 can obscure clinically relevant information. The CT reconstruction in pane A) represents a situation where no artifacts are present. This is contrasted by pane B) where streak artifacts occur after insertion of a metal coil into a vessel of a human brain to treat an aneurism. Pane C) shows another streak artifact in reconstructed imagery where a part of a stent is obscured by streaks caused by an implanted metal coil.

In broad terms, the proposed imaging processing system IPS is configured to indicate areas that are potentially affected by streak artifacts in a single (or a few) input projection image, prior to acquiring all the projection images necessary for reconstruction. In CT, a scout image may be used as the input image for indicting therein the artifact affected area(s). The user can then reposition the patient and/or plan a different trajectory to avoid having artifacts in critical areas of interest. Once suitable repositioned or once a suitable trajectory has been selected, the remaining projection images can be acquired and they are then passed on to the reconstructor RECON to perform the reconstruction. In this way, the chances that important information is obscured by artifacts are considerably lower. This can lead to i) less radiation dose for the patient, since scans do not need to be retaken and ii) better diagnosis, since critical information is not obscured by streak artifacts.

More particularly and with reference to the right part in FIG. 1, the (one or more) input projection image is received at input port IN. This input image may be a single projection image or maybe formed from a more than one projection images that are required with the X-ray imaging apparatus IM. The input image is then analyzed by an image artifact extent predictor AP. Predictor AP is configured to predict in the input image a projection area of an artifact as it would appear in a reconstruction if one were to reconstruct from projection images using the rotation plane as per the current input image.

As will be explained in more detail below at FIGS. 4 and 5 this prediction is based on an identification of the footprint of radiation-opaque objects obtained in a segmentation. Since the intended trajectory of the rotational image acquisition in respect of the X-ray image is known, an orientation and/or extent of a streak artifacts caused by the radio opaque object in a reconstruction can be predicted.

In an embodiment, this information can be output on a monitor MT as a visual feedback via visualizer VIZ. For instance, a visual indicator for said area can be overlaid on the input X-ray image. In this context, CBCT is advantageous over fan beam CT, as the projection image in CBCT is a 2D radiograph which can be rendered directly for view with the indicator overlaid.

Figure 3:
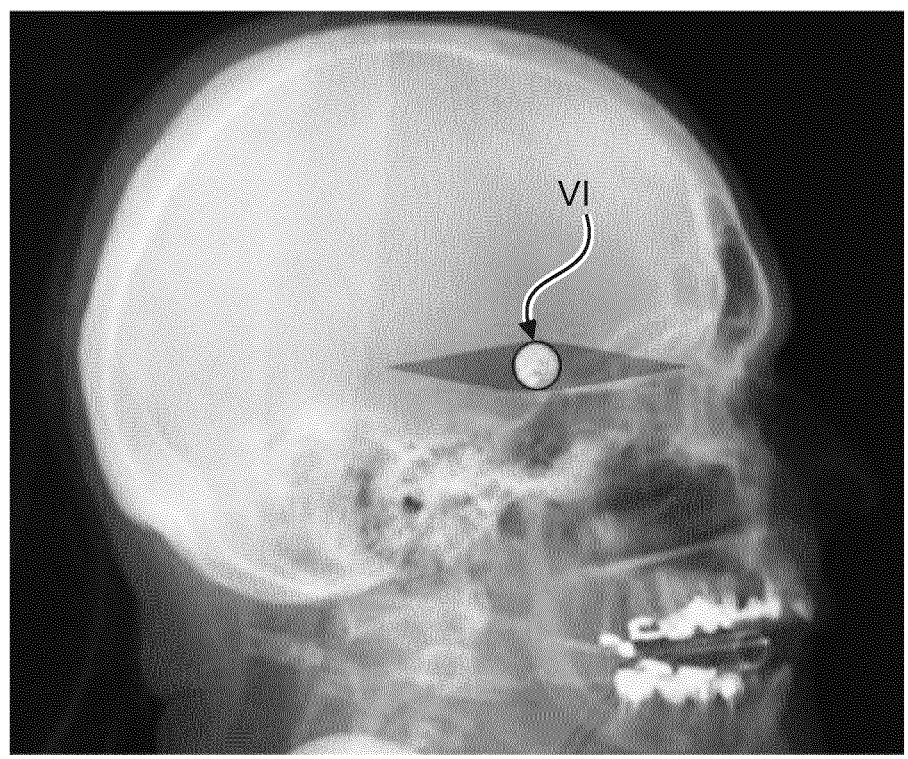
FIG. 3 shows a visual indication overlaid on an image to indicate an extent of a reconstruction artifact.

FIG. 3 shows a visual output according to one embodiment as produced by the visualizer VIZ. As briefly mentioned above, the visual indicator VI indicates the predicted projection area affected by streak artifacts caused by the highly radio-opaque object. Further, the image shown by the visualizer VIZ enables a user to identify an area of intersection between the artefact projection and a region of interest as guidance in selecting a potential adjustment for the spatial configuration.

A graphical user interface GUI may be provided in which the user can select different orientations or inclinations for the rotation plane and thereby determine the adjusted spatial configuration The predictor AP and the visualizer VIZ may then co-operate to update the visual indicator in the input image accordingly and the visual indication then shows the intersection area between the region of interest and a projection of a reconstruction artefact as it would appear if the newly specified rotation plane were to be used for the acquisition of projection images.

The updated or adapted visual indictor may be displayed together with the current image or a new projection image in the newly specified imaging geometry can be acquired and the adapted visual indicator is displayed together with the newly acquired image.

An imaging geometry adjuster PA is configured to determine an adjustment for instance of the orientation, direction or tilt of the rotation plane so that the disturbance by the streak artifact on the pre-defined region of interest is mitigated or reduced. More particularly, a geometrical intersection between the predicted projection area and the area that corresponds to the region of interest is decreased, when the adjusted imaging geometry is selected and effectuated.

The adjuster PA may carry out a simulated determination of one or more adjusted imaging geometries, and subsequently also control a physically adjustment of one or more system components so as to effectuate an actual adjustment of the imaging geometry.

In an embodiment, the predictor AP may then determine an updated projection area of a reconstruction artefact in a simulated adjusted spatial configuration. The prediction and adjustment determination may be repeated until a desirable geometry has been found.

Thus, a physical movement of components of an imaging system, for example a C-arm movement, is only required once a desirable imaging geometry, for example a rotation plane in which reconstruction artefacts in the region of interest will be reduced, has been identified.

The above introduced components such as an input port, the visualizer, the adjuster and the graphical user interface can be implemented as functional modules that are run as software routines on a data processing unit PU such as a general purpose computer. For instance, the software routine may run on a work station associated with the imager IM or with a group of imagers in a network. Implementations of the components other than in software are also envisaged and include field programmable field arrays (FPGA) or integrated circuits (IC) or others.

The visual indication shown in FIG. 3 of the projection area has roughly the shape of a lozenge or diamond. This shape is a consequence of the manner of which the projection area is computed as will be explained further below with reference to FIGS. 4 and 5. Other shapes of the visual indicator however are also envisaged herein. Preferably, however, the visual indicator VI for the projection area has a directional component to be able to intuitively indicate to the user a main orientation or main direction of the streak artifacts. The footprint of the radiation-opaque element may also be indicated graphically such as a circle as shown in the FIG. 3 but other shapes are also envisaged. As will be appreciated by continued reference to FIG. 3, the visual indicator in one embodiment has a compass needle appearance. However, other suggestive symbology capable of encoding direction is also envisaged herein. Yet further, the visual indication VI may be rendered as color-coded to better offset against the background. In other embodiments, the visual indicator VI merely outlines contours of the streak artifact affected area to minimize obstruction of underlying image information.

Rather than using the same color-coding, the segmentation of the high opacity object may itself be color coded in a different color from the one used for the symbology that is indicative of the projection area.

Figure 4:
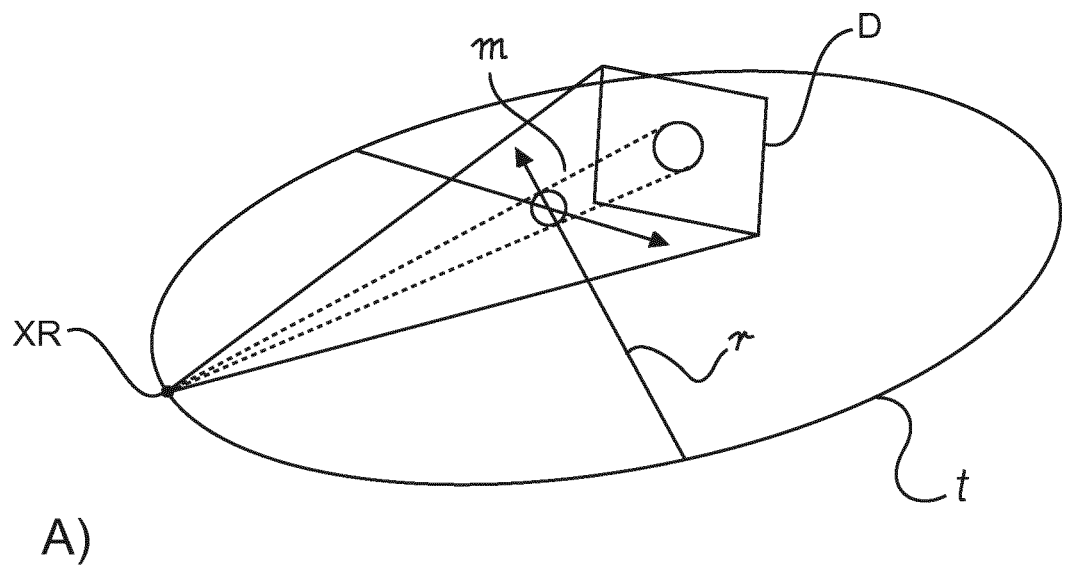
FIGS. 4 and 5 illustrate the underlying geometry for constructing the visual indication.
Figure 4:
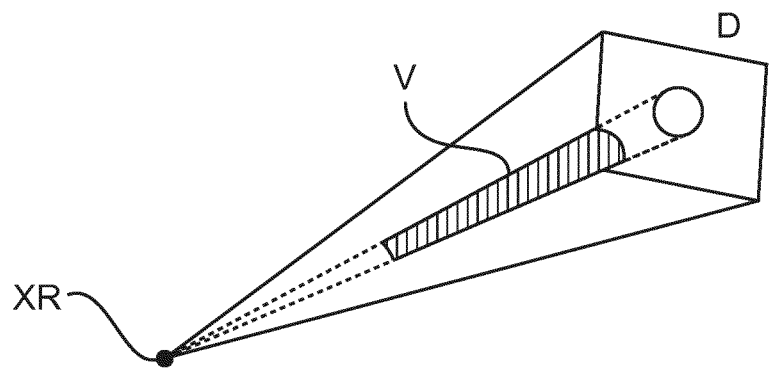
Figure 5:
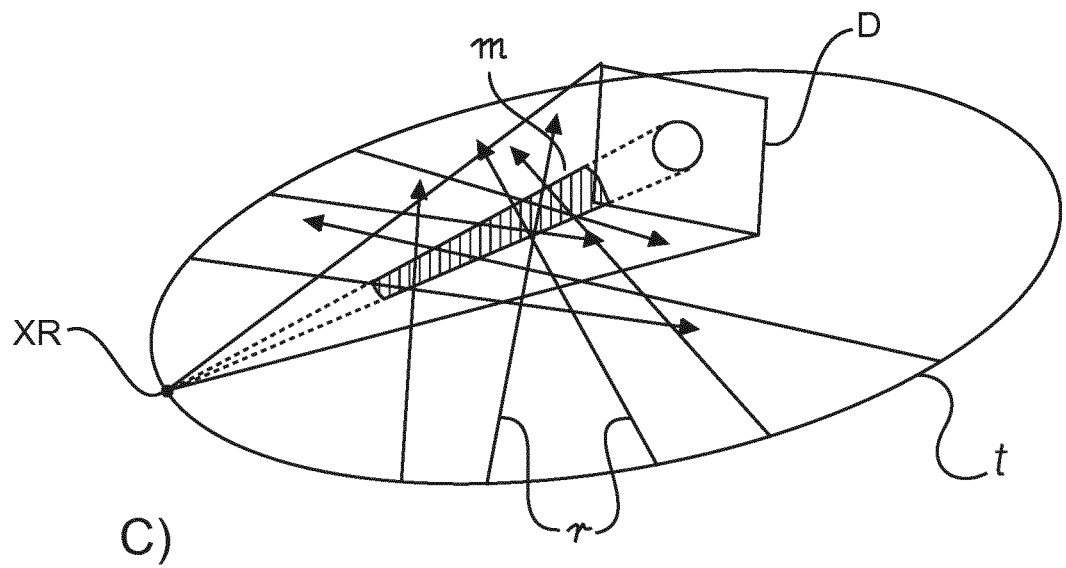
Figure 5:
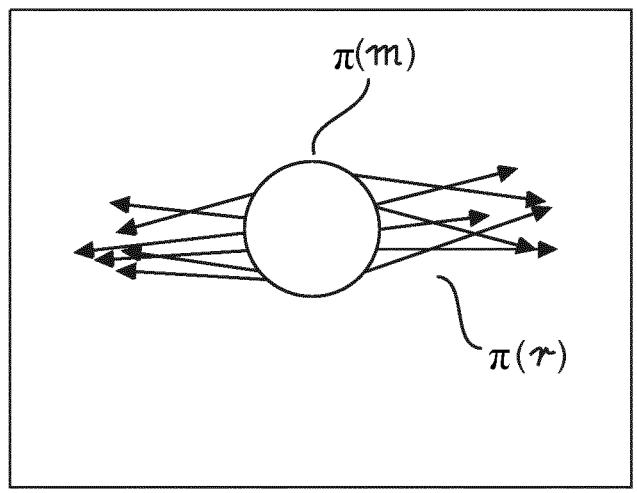

Referring now in more detail to FIGS. 4 and 5, these are illustrations of the operation of the projection area predictor AP. In particular, FIG. 4 or 5 are illustrations of the underlying algorithmic steps for computing shape and/or extent of the predicted artifact inflicted projection area. At this stage it will be useful to recall same geometry in relation to the rotation plane. The X-ray geometry determines a trajectory traced out during the projection image acquisition. For simplicity, let's assume this trajectory is circular. A virtual line can be defined from a focal spot of the X-ray source XR to the detector's D center. When this line is followed during the circular trajectory, a virtual disk in the rotation plane is defined. For any X-ray projection image taken from a position on the circular trajectory, the virtual disk can be projected as a line on the X-ray projection image (such as one acquired by a CBCT). This line defines the main orientation of the streak artifacts that would be caused by the radiopaque object in a reconstruction. And it is the course of this line relative to the ROI in the image that can be changed by changing the imaging geometry, e.g. changing the rotation plane or changing the position/tilt of the patient support C.

Referring now first to FIG. 4A), this shows an illustration of the rotation plane now shown for ease of representation horizontally rather than vertically. For each position of the X-ray source XR on the trajectory t, the radiation can be thought of as propagating along rays r that emanate from the focal spot towards the detector at the given position on the trajectory. The rays form respective cones in the surrounding space.

Any of the rays r that pass through, say, a metal object m, can cause streak artifacts in the 3D reconstruction. As indicted in FIG. 4B), a single projection image does not provide enough information to determine where exactly the metal object m is located, but at least a volume V (a cone segment) including the object can be determined.

As shown in FIG. 5C), given the location of such a volume V as an estimate for the 3D location of the object m, it is matter of simple geometry to determine all possible streak paths r through this volume V.

As shown in FIG. 5D), forward projecting these paths Π(r) and the footprint Π(m) of the object m onto the input image plane together then furnish a definition for the predicted artifact inflicted area. As a refinement, the geometric hull of this area can be constructed to define the visual indicator VI. It should be clear from FIG. 4B) that using two or more projection images (acquired at angles sufficiently apart) can be used to reduce the location volume V thus improving the accuracy of the prediction. The artifact inflicted area can be displayed with the input image or with a new image acquired in a new imaging geometry.

In sum, and as shown in FIG. 5D), the predicted area affected by reconstruction artifacts is formed by the combined projection footprint of the highly radiopaque object and the projections of the individual rays through an estimated location of the object. The combination or conglomerate of these individual footprints then forms an area from which the projection area indicative of the reconstruction artifacts can be constructed. In one embodiment, a boundary of the predicted artifact inflicted area is defined by an envelope curve (e.g., a convex hull) around the combined projection footprints.

As a further refinement for defining the predicted area, in one embodiment, from any border pixel on the footprint of the radiopaque element, an extent of the streaks can be predicted using the main orientation vector and the length of the intersection with the footprint of the radiopaque object. The length of the intersection is defined by the intersection of a line passing through this border point along the main orientation vector and the radiopaque object footprint m. In this manner, an area in the input projection image affected by the streaks can be predicted. A visualization of this will be similar to the visual indictor VI of FIG. 3. In other words, a contribution to the final prediction area of a given ray r passing through a possible location volume V is weighted by the estimated length of the intersection. The weighting of said contributions can be rendered graphically by different color/grey values or opacity. This can be implemented by a weight function in dependence on path length through the location volume V for object m. For example, a ray that passes through 1 mm of metal does not have the same impact as a ray passing through 10 mm of metal. By "impact" we refer to the visual distinctness with which such rays contribute to the reconstruction artifact. The weighting function does not necessarily need to be proportional to the estimated length, since at some point the photon information is completely starved off. For instance, a 30 mm path length might have the exact same impact as 60 mm. In other words, the weight function is proportional (not necessarily linearly) with path length through location volume V up to a cut-off length from which point onwards the weight function remains constant.

Now, once the predicted projection area has been established as explained above at FIGS. 4,5, in an embodiment a visual indication VI of the predicted area can be rendered graphically on the display unit MT. The user can then visually examine whether the artifact extends into or overlaps with a pre-defined region of interest ROI.

Alternatively, this evaluation can be carried out automatically by the adjuster PA.

As soon as there is no or suitably reduced overlap between the projection of the artefact and the region of interest ROI, the user can continue to activate the imager IM to acquire the projection images necessary for a CBCT scan. The acquired projection images are then forwarded to the re-constructer and the reconstruction commences to produce the volumetric image.

However, if the evaluation reveals that indeed the reconstruction artifact would compromise the image quality at the ROI at an unacceptable level, the proposed system IPS allows the user to choose, based on the visual indication VI a new imaging geometry at which the projection images for reconstruction should be collected. The new imaging geometry can be achieved as explained earlier by rotating the rotation plane around an axis parallel to that plane or by shifting or tilting the support C on which the object to be imaged P resides.

As said, an adjusted imaging geometry may be chosen automatically by an imaging geometry adjuster PA. In this case, the predictor AP may receive a (simulated) adjusted geometry from the adjuster PA, so that reconstruction artefacts according to the new geometry can be predicted and used in a subsequent evaluation. Thus, a minimum intersection between artefact projections and the region of interest may be determined in an iterative process.

More particularly, an alternative rotation axis can be defined to realize a tilted trajectory. This tilted trajectory can be effectuated by either changing the angulation of the X-ray system while rotating which results in a tilted trajectory, or by tilting the patient table. The tilted trajectory will then still pass through the iso-center. The tilting angle can be selected by the user or automatically.

In the embodiment for automatic determination of a new rotation plane, the ROI (e.g., a stent) is segmented, either automatically by an appropriate algorithm, or semi-automatically. It can be segmented in the input image, such as a prior CBCT image or in a 2D X-ray radiograph of a C-arm system. The rotation axis of the current rotation plane for the rotational trajectory is then modified in a loop in suitable increments until the streaks no longer intersect with the segmented ROI. For instance, the rotation plane that results in the least streaks within the ROI is then chosen. If there are multiple such planes that fit this criterion, then the one which would incur the least such modification is chosen. For instance, a tilt angle of the current rotation plane can be changed by rotating the current rotation axis in increments whilst examining how the intersection area between streaks projection are and ROI changes to find a better rotation axis.

Turning now to the manual embodiment, the following variants are envisaged. In one embodiment, the user enters numerically a tilt angle. Alternatively, an input tool such as a computer mouse may be used to change the tilt of the trajectory, e.g. by selecting tilt angle values from a list, etc. Graphical-geometrical input is also envisaged where the user uses a mouse or other input tool to draw in the input image a line indicating the desired orientation and location of the intersection of the rotation plane with the plane of the X-ray image.

Figure 6:
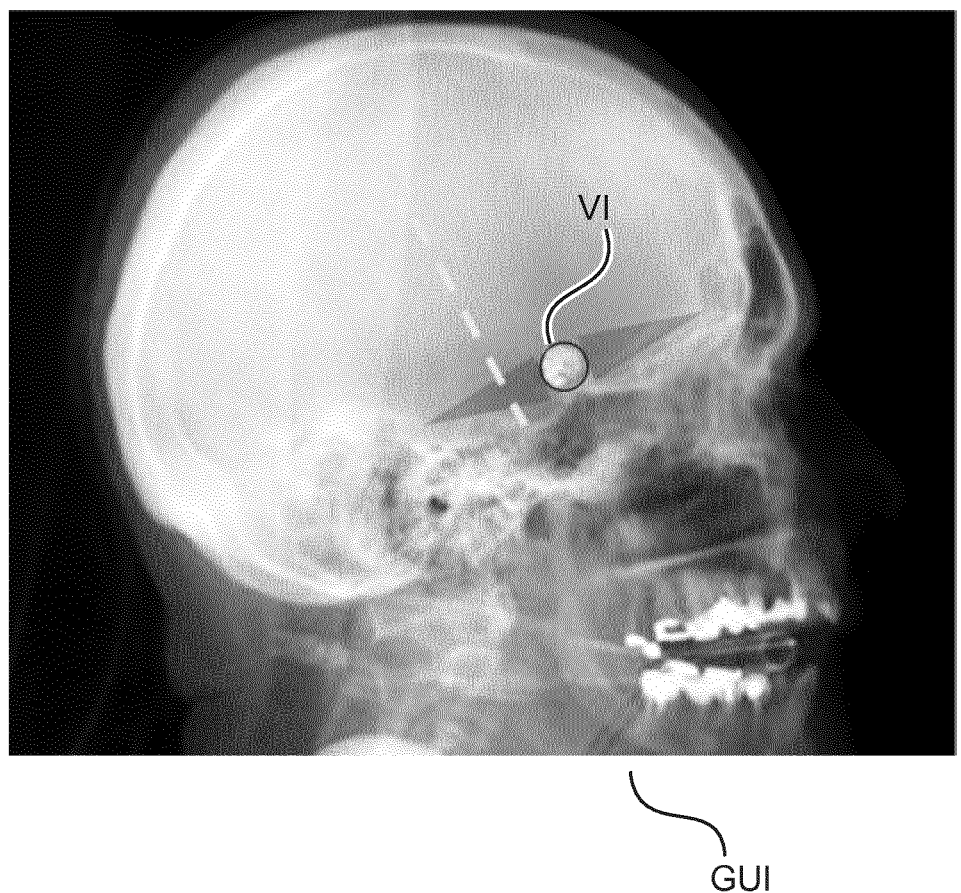
FIG. 6 shows a graphical user interface for specifying a new rotation plane in a rotational imaging system.

Reference is now made to FIG. 6 which shows an exemplary embodiment for a suitable user interface, for instance a graphical user interface GUI. The dashed line shows a user specified intersection of the rotation plane with the plane of the image. The specification can be done defined interactively by the user by using a computer mouse to define a new intersection line by specifying two points in an otherwise known manner. Another option is to use a touch screen and the user can use finger touch instructions to define the intersection line of the new rotational plane. When using touch screen interaction the user can either draw a new intersection line on the screen by dragging their finger across the screen from one position to another or the user simply specifies two points and the system will automatically interpolate the intersection line therefrom. Other graphical or non-graphical input mechanisms are also envisaged herein.

Once the user has specified the new rotation plane, the system IPS issues a suitable command or event which is intercepted by an event handler which in turn instructs the predictor AP to now re-predict the projection area based on the newly defined rotation plane and this projection area is then displayed on the screen by visualizer VIZ instead of the currently displayed projection area indication mark VI. The user can thus "experiment" with the system to find a suitable rotation plane which will result in artifact orientation or extent which will affect the ROI to a lesser degree than in the current imaging geometry.

Alternatively and inversely to the embodiments above, the user may specify graphically or otherwise the main orientation of the streak artifacts in the input X-ray image. The system then computes the required imaging geometry change associated with the specified main orientation of the streak.

As mentioned earlier, once a satisfactory imaging geometry has been found the imaging apparatus IM then commences to acquire the necessary projection images at the so specified imaging geometry. The imaging acquisition at this imaging geometry can be triggered either automatically or upon the user issuing a suitable control signal from the operation console OC.

Figure 7:
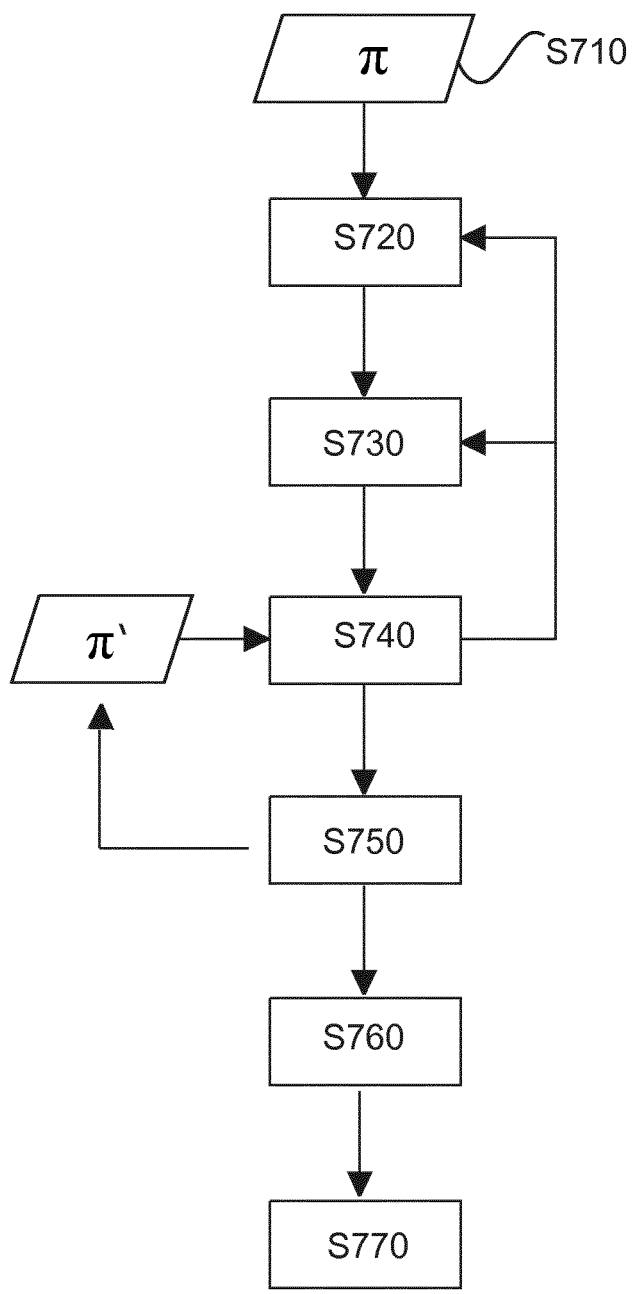
FIG. 7 shows an image processing method.

Reference is now made to flow chart FIG. 7 which shows an image processing method as implemented by the image processing system in FIG. 1. It will be understood however that the following explanation in terms of method steps is not necessarily tied to the architecture as per FIG. 1. In other words, the following method steps constitute a teaching in its own right.

At step S710 a single or two or more input projection images of an object P to be imaged are received. The image is acquired by a rotational image apparatus IM. The input projection image is acquired at a position on an imaging trajectory in current rotation plane around the imaging region. Alternatively, in a CT setting, a scout image compiled from a plurality of projection images may be used as the input image.

At step S720 a projection area is then predicted for said input image. The prediction is based on the current geometry as per the current rotation plane. The projection area defines an extent or a main direction of a reconstruction artifact. The reconstruction artifact is one that would result if one were to perform a reconstruction based on projection data acquired in the current imaging geometry. The artifact is induced in the reconstruction due to the presence in the imaging region of a high opacity object m, such as a metal object.

In one embodiment, the prediction is based on a segmentation for the footprint of the high opacity object m. The radiopaque object footprint in the input X-ray image can be found by applying a image value thresholding. Since the size of the object also impacts the streak artifacts, an additional criterion can be used to segment only object footprints of a certain minimal size. Alternatively, a function that adapts the threshold based on the size of the found object can be used. Yet alternatively, another segmentation approach can be used, e.g., the watershed algorithm, region growing, manual annotation, graph cuts, etc. As a further alternative, the high-radiopaque object footprint is segmented in a prior CT or CBCT, and the segmentation is then forward-projected onto the input 2D X-ray image(s).

Rays through a location volume for said object are forward-projected onto the input image and are combined with the footprint of the object m to so obtain a definition of an area likely to be inflicted by artifacts in a reconstruction. More particularly, the artifact inflicted area can be defined as explained above at FIGS. 4 and 5.

A visualization of the predicted projection area on a display unit is effected at optional step S730.

At step S740, a specification of a change of the imaging geometry is determined and in response to this optionally the visual indication may be adapted. In one embodiment, a specification of a new rotation plane π' relative to the object to be imaged is received by specifying a new rotation axis α'. The specification may include a proposed tilting of the rotation plane. More generally, a new rotation axis for the rotation plane is specified.

The change can be requested automatically or by the user, in dependence of an intersection between the predicted projection area and an area in the image that corresponds to a predefined region of interest ROI.

The specification may alternatively include a tilting or shifting of the support on which the object resides during imaging.

In response to the specification for an imaging geometry change, the previous steps S720 and S730 of predicting and (optionally) visualizing may be repeated. In other words, based on the newly determined adjusted imaging geometry, an updated visual indication for a newly predicted area for the artifact orientation and/extension is computed. The updated or adapted visualization can be displayed on the input image or on a new input image acquired at the newly specified imaging geometry.

In a step S750, a determined adjusted imaging geometry is effectuated, thus a movement of one or more system components is controlled so as to reposition the system in accordance with the new imaging geometry. That is, under this geometry, when reconstructing from projection data collected in this new geometry, the ROI would be completely free from visual interference with streak artifacts or at least this interference is below a user perceivable level. Once the final new geometry has been found, the corresponding projection area can be visualized as per step S740.

At step S760, once the new geometry has been set, the imaging apparatus operates to acquire projection images at the new imaging geometry. For instance, the X-ray source traces out different positions on a trajectory in a newly adjusted imaging plane around the object.

At step S770 the so acquired projection imagery is then reconstructed by a suitable reconstruction algorithm (analytic or iterative) into a desired volumetric image of the object, in particular of the region of interest.

In sum, it is proposed herein to avoid or at least reduce streak artifacts in reconstructed images. At least one input X-ray image is acquired before the actual scan. In this input image, radiopaque areas are identified. Then, based on knowledge of the trajectory of the planned rotational scan, orientation of streaks in reconstruction from the planned acquisition may be predicted. This information is provided in one embodiment as visual feedback to the user, preferably in the input X-ray image. Based on the information, a new rotational scan trajectory may be determined. For example, the user may specify graphically or not an alternative rotation axis. Streak artifacts in the corresponding newly proposed scan trajectory may again be predicted and visualized. An alternative trajectory may also be determined automatically by simulating streak artifacts for a range of tilt angles and choosing the tilt angle that has least streaks within the object of interest.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
   an input port for receiving a projection image of an object, the projection image having been acquired by a rotational image apparatus at a position on an imaging trajectory in a first rotation plane (π) around an imaging region;
   an image artifact extent predictor configured to determine, for said projection image, a prediction of a projection area of a reconstruction artifact, said prediction being based on an identification of a footprint of a radiation-opaque object resident in the imaging region; and
   an imaging geometry adjuster configured to determine an adjustment of a relative spatial configuration between said first rotation plane and the object so as to reduce an intersection between the predicted projection area and an area in the image that corresponds to a predefined region of interest.

2. The image processing system of claim 1, wherein the imaging geometry adjuster is configured to adjust said spatial configuration by defining an adjusted rotation plane having a different rotation axis than the first rotation plane.

3. The image processing system of claim 1, further comprising a visualizer configured to provide, to a display unit, image information comprising said image together with a visual indication of the projection area of the reconstruction artefact.

4. The image processing system of claim 3, wherein the visualizer is further configured to provide a visualization of the predicted projection area of the reconstruction artifact for an adjusted spatial configuration.

5. The image processing system of claim 1, wherein said reconstruction artifact is caused by the radio-opaque object, in particular a metal object, resident in the imaging region.

6. The image processing system of claim 1, wherein said specified change of the spatial configuration is effectuated by a human user.

7. The image processing system of claim 1, comprising a graphical user interface configured to allow the user to graphically specify an adjustment of the relative spatial configuration between the object and the rotation plane.

8. An imaging arrangement, comprising the image processing system of claim 1;
   an imaging apparatus for acquiring a projection image; and
   a display unit for receiving and displaying the image information from the visualizer.

9. An imaging arrangement according to claim 8, wherein the imaging geometry adjuster of the image processing system is configured to instruct the imaging apparatus to carry out an adjustment of the rotational plane.

10. An image processing method, comprising the steps of:
    receiving a projection image of an object, the image acquired by a rotational image apparatus at a position on an imaging trajectory in an adjustable rotation plane around an imaging region;
    predicting, for said projection image, a projection area of a reconstruction artifact, wherein said prediction is based on an identification of a footprint of the radiation-opaque object resident in the imaging region; and
    determining an adjustment of a relative spatial configuration between said first rotation plane and the object so as to reduce an intersection between the predicted projection area and an area in the image that corresponds to a predefined region of interest.

11. The image processing method of claim 10, wherein the predicting step and the determining step are repeated so as to iteratively reduce said intersection.

12. The image processing method of claim 10, comprising:
    effectuating a determined adjustment in the relative spatial configuration between said rotation plane and the object.

13. The image processing method of claim 12, further comprising the steps of:
    operating the imaging apparatus to acquire projection images at different positions on a trajectory in accordance with an adjusted relative spatial configuration between the rotation plane and the object; and
    reconstructing from the acquired projection images a volumetric image of at least the region of interest.

14. A non-transitory computer-readable medium having stored thereon a computer program element for controlling a system, which, when being executed by a processing unit is adapted to perform the method steps of claim 10.

* * * * *